United States Patent
Kawabori

(10) Patent No.: US 12,017,040 B2
(45) Date of Patent: Jun. 25, 2024

(54) PUNCTURE NEEDLE, PUNCTURE NEEDLE KIT, AND STEREOTACTIC BRAIN SURGERY DEVICE

(71) Applicant: RAINBOW INC., Hokkaido (JP)

(72) Inventor: Masahito Kawabori, Hokkaido (JP)

(73) Assignee: RAINBOW INC., Sapporo (JP)

( * ) Notice: Subject to any disclaimer, the term of this patent is extended or adjusted under 35 U.S.C. 154(b) by 91 days.

(21) Appl. No.: 17/614,046

(22) PCT Filed: May 29, 2020

(86) PCT No.: PCT/JP2020/021373
§ 371 (c)(1),
(2) Date: Nov. 24, 2021

(87) PCT Pub. No.: WO2020/241833
PCT Pub. Date: Dec. 3, 2020

(65) Prior Publication Data
US 2022/0233767 A1 Jul. 28, 2022

(30) Foreign Application Priority Data

May 31, 2019 (JP) ................................ 2019-102123
Dec. 4, 2019 (WO) .................. PCT/JP2019/047526

(51) Int. Cl.
*A61M 5/158* (2006.01)
*A61B 90/11* (2016.01)
(Continued)

(52) U.S. Cl.
CPC ............. *A61M 5/158* (2013.01); *A61B 90/11* (2016.02); *A61B 90/14* (2016.02); *A61M 5/34* (2013.01);
(Continued)

(58) Field of Classification Search
CPC ........ A61M 5/158; A61M 5/34; A61M 25/06; A61M 25/065; A61M 2210/0693; A61M 5/32; A61M 5/3291; A61M 5/30
See application file for complete search history.

(56) References Cited

U.S. PATENT DOCUMENTS 4,681,103 A 7/1987 Boner et al.
7,137,969 B1 * 11/2006 Mendez ............ A61B 17/3403
604/207

(Continued)

FOREIGN PATENT DOCUMENTS

CN 108578883 A 9/2018
GB 2262238 A 6/1993
(Continued)

OTHER PUBLICATIONS

International Search Report for related International Application No. PCT/JP2020/021373 dated Aug. 11, 2020 and its English Translation.
(Continued)

*Primary Examiner* — Robert J Utama
*Assistant Examiner* — Neeraja Gollamudi
(74) *Attorney, Agent, or Firm* — Renner, Otto, Boisselle & Sklar, LLP

(57) ABSTRACT

The objective of the present invention is for an object discharged from a discharge port to be less liable to form a jet flow, and less liable to cause injury to the central nervous system. A passage 11 for a cell is formed inside a needle body 10 of a puncture needle 1. A discharge port 15 for a cell is formed in a side surface 13b of a front end part 13 of the needle body 10. Furthermore, the needle body is a single tube provided with a passage for an object. Further, a discharge path 14 for a cell, oriented upward from the passage 11 toward the discharge port 15, is formed in the front end part 13. The discharge path 14 comprises a
(Continued)

frustoconical part 14a and a columnar part 14b. As a result, the discharge path 14 is formed in such a manner that the surface area of a cross section orthogonal to the upward/downward direction increases smoothly towards the discharge port 15 in at least one part of the discharge path 14, and, in each position in the upward/downward direction, is equal to or greater than the surface area of a cross section in a position closer to the passage 11.

2 Claims, 13 Drawing Sheets

(51) Int. Cl.
   *A61B 90/14* (2016.01)
   *A61M 5/34* (2006.01)
(52) U.S. Cl.
   CPC . *A61M 2202/09* (2013.01); *A61M 2210/0693* (2013.01)

(56) References Cited

U.S. PATENT DOCUMENTS

| | | | |
|---|---|---|---|
| 2002/0007149 A1* | 1/2002 | Nelson | A61M 5/30 |
| | | | 977/956 |
| 2002/0055729 A1 | 5/2002 | Goll | |
| 2003/0045842 A1 | 3/2003 | Kawakita et al. | |
| 2005/0275136 A1 | 12/2005 | Haindl | |
| 2010/0324535 A1* | 12/2010 | Triel | B29C 67/0048 |
| | | | 428/36.9 |
| 2012/0083742 A1* | 4/2012 | Nelson | A61B 90/11 |
| | | | 604/175 |
| 2012/0265168 A1 | 10/2012 | Horowitz et al. | |
| 2013/0066266 A1 | 3/2013 | Cunningham | |

FOREIGN PATENT DOCUMENTS

| | | | | |
|---|---|---|---|---|
| JP | 11276594 | | 10/1999 | |
| JP | 2005535383 | A | 11/2005 | |
| JP | 201220042 | A | 2/2012 | |
| JP | 2013536020 | A | 9/2013 | |
| JP | 5665027 | | 12/2014 | |
| WO | WO-02083228 | A2 * | 10/2002 | A61M 5/158 |
| WO | 2004014233 | A1 | 2/2004 | |
| WO | 2012021336 | A1 | 2/2012 | |
| WO | 2018125829 | A1 | 7/2018 | |
| WO | WO-2018125829 | A1 * | 7/2018 | A61K 35/28 |

OTHER PUBLICATIONS

Kawabori, Masahito et al., "Evaluation of Novel Stereotactic Cannula for Stem Cell Transplantation against Central Nervous System Disease", Stem Cells International, vol. 2020, Article ID 4085617, [online], Feb. 11, 2020, [retrieval date Aug. 3, 2020], pp. 1-8.
First Office Action for corresponding Japanese Application No. 2020-558649 dated Jan. 5, 2021 and its English Machine Translation.
Second Office Action for corresponding Japanese Application No. 2020-558649 dated May 24, 2021 and its English Machine Translation.
Extended European Search Report, including the Supplementary European Search Report and the European Search Opinion for corresponding European Application No. 20814398.2 dated Dec. 21, 2022.

* cited by examiner

[Figure 1]
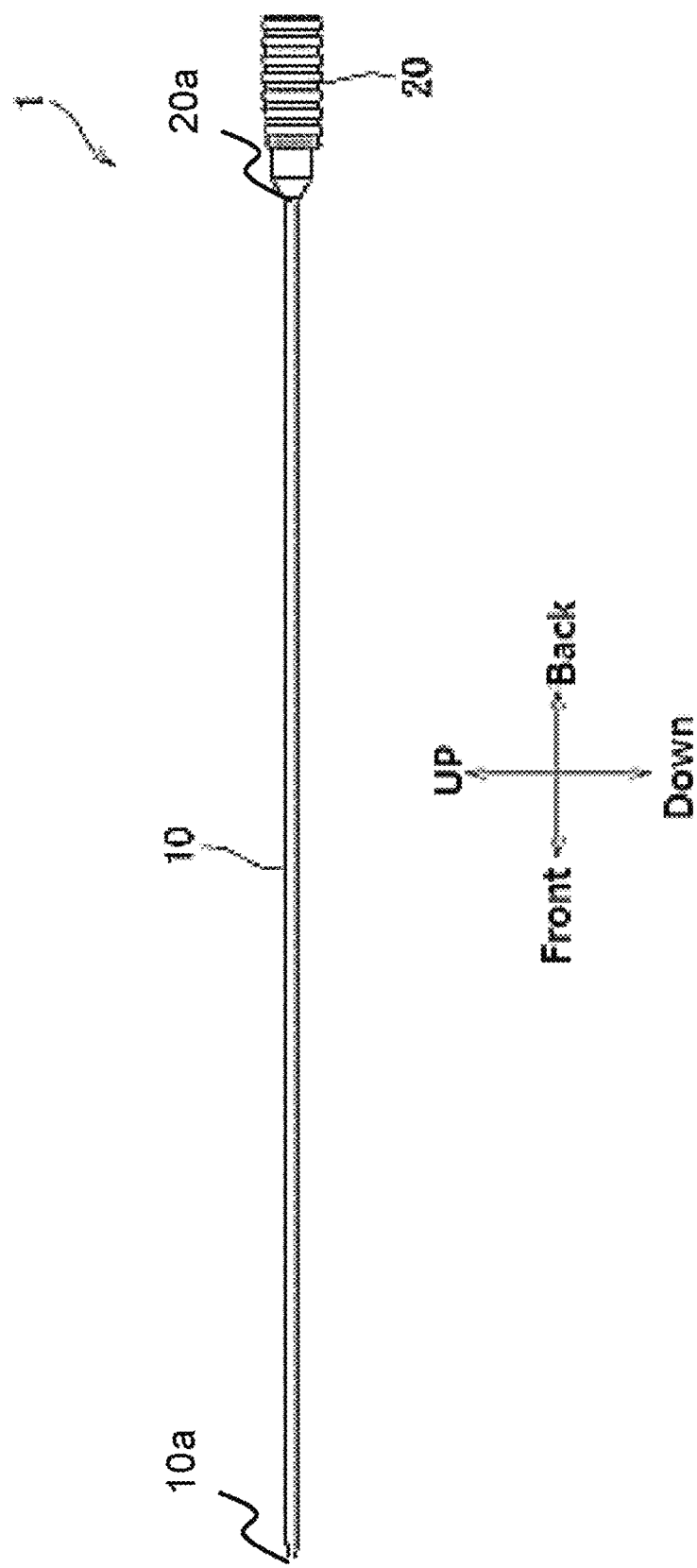

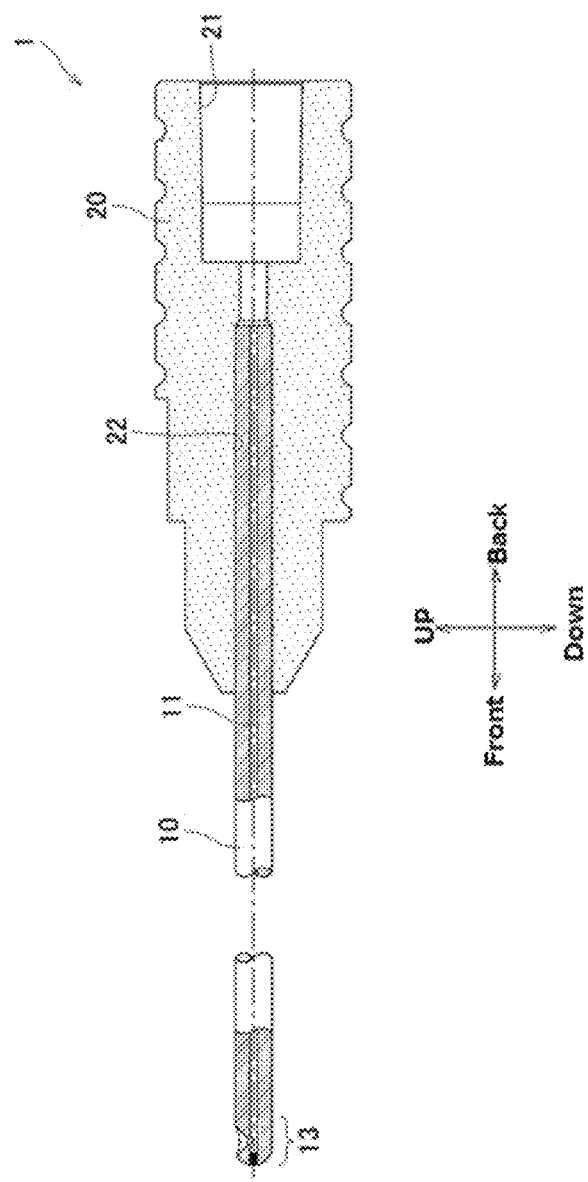
[Figure 2]

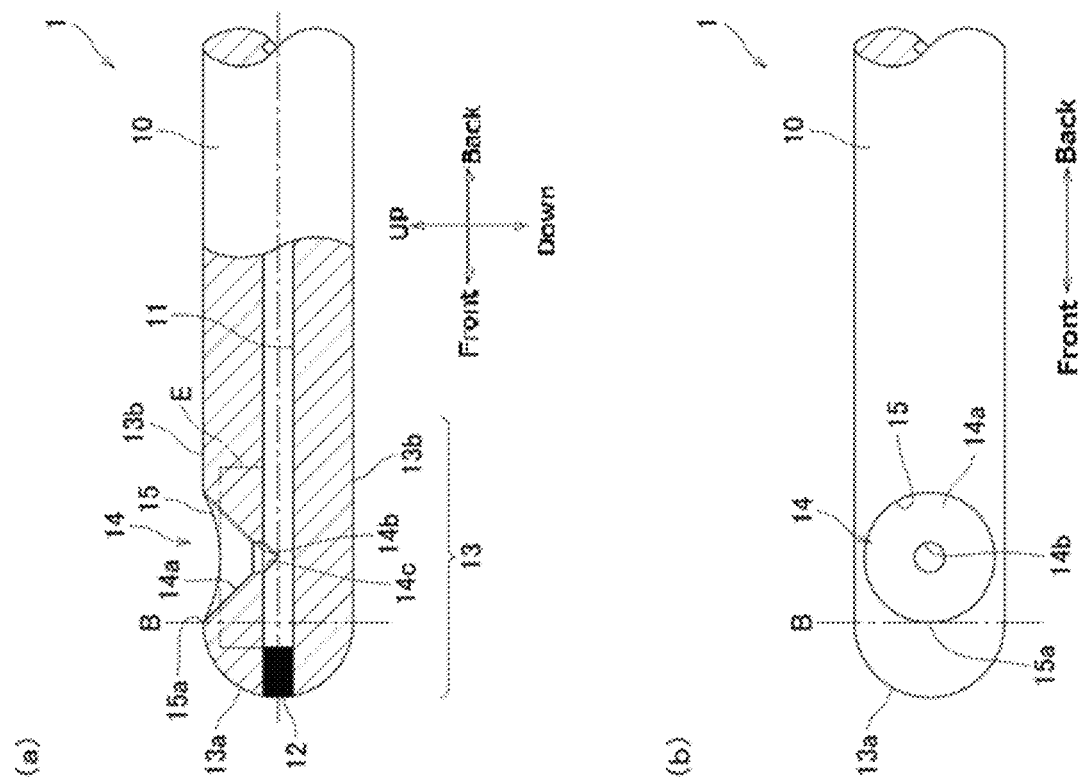
[Figure 3]

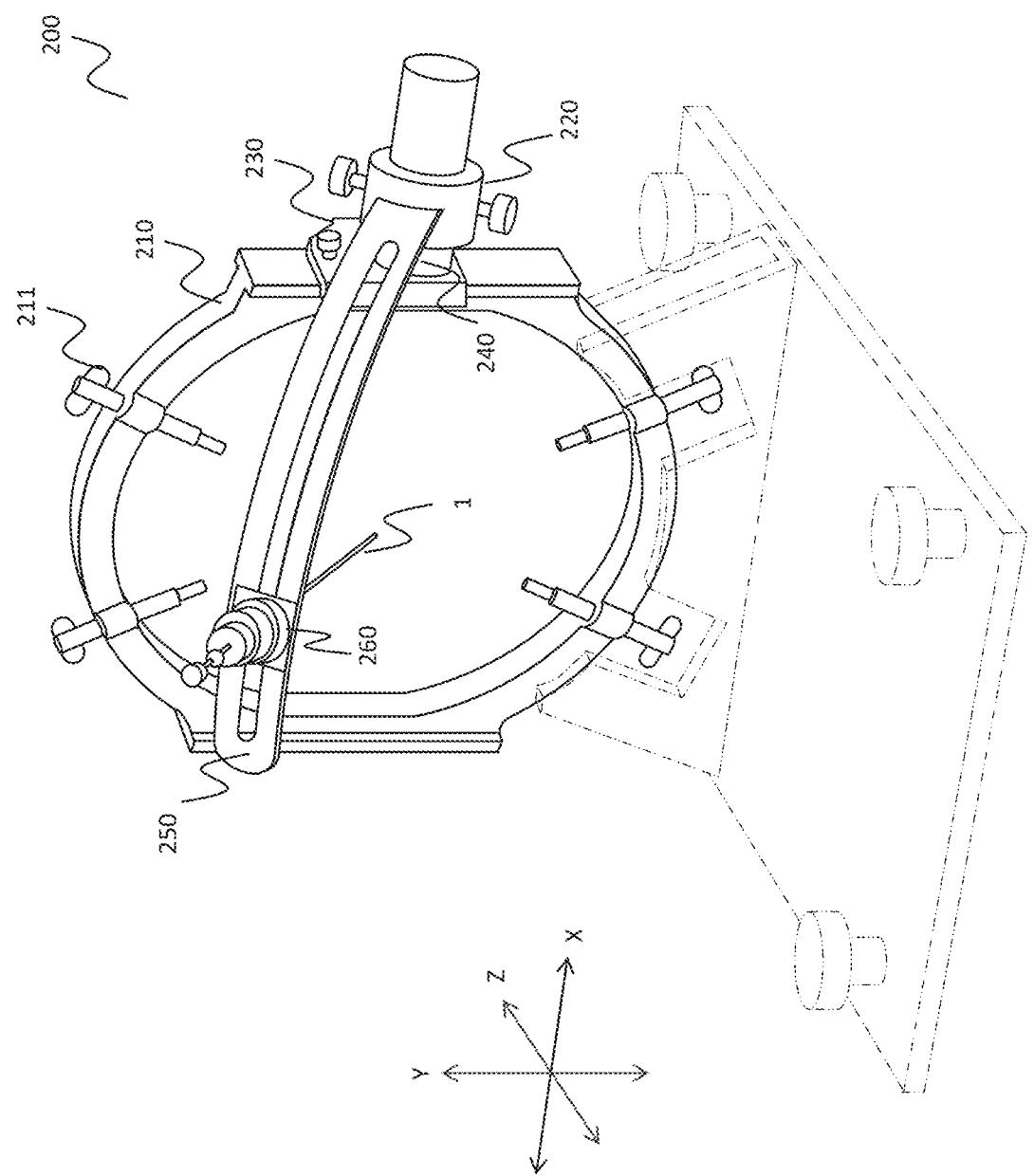
[Figure 4]

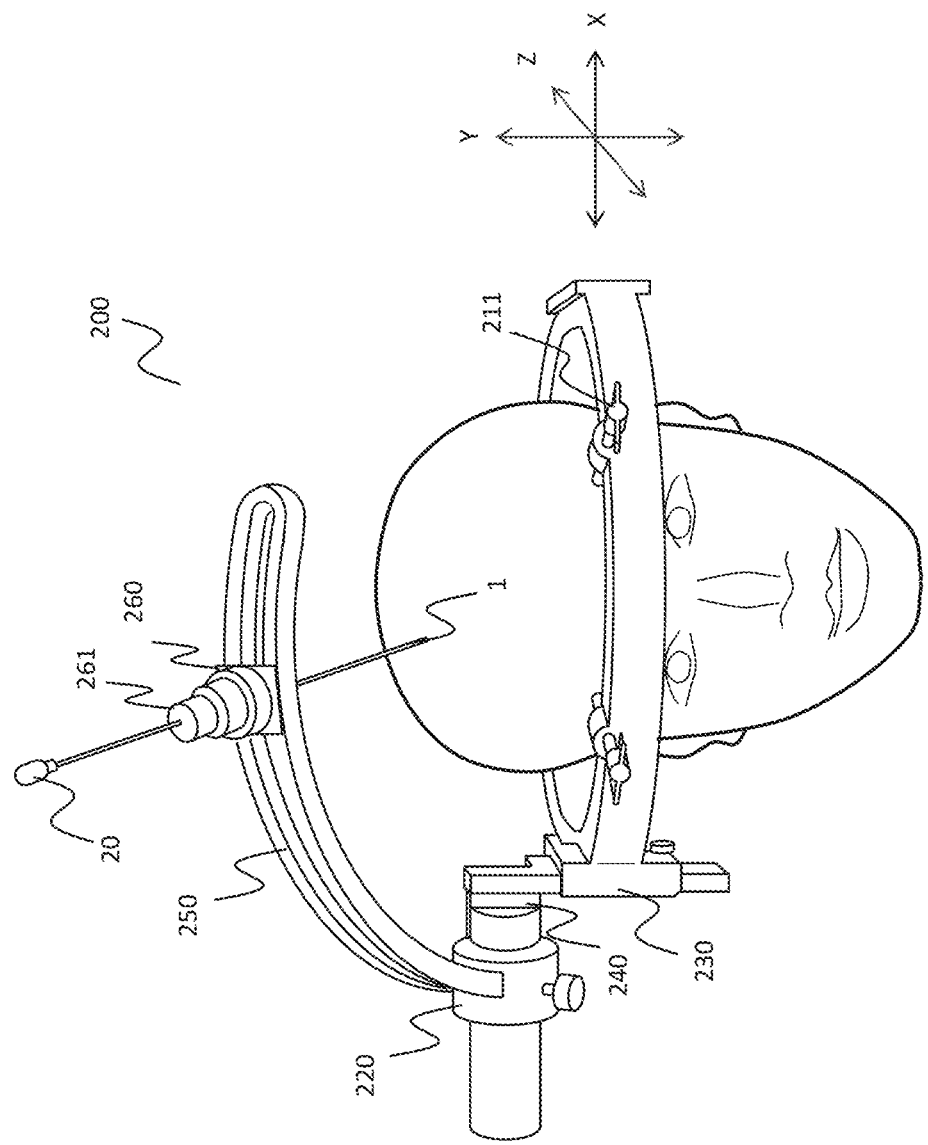
[Figure 5]

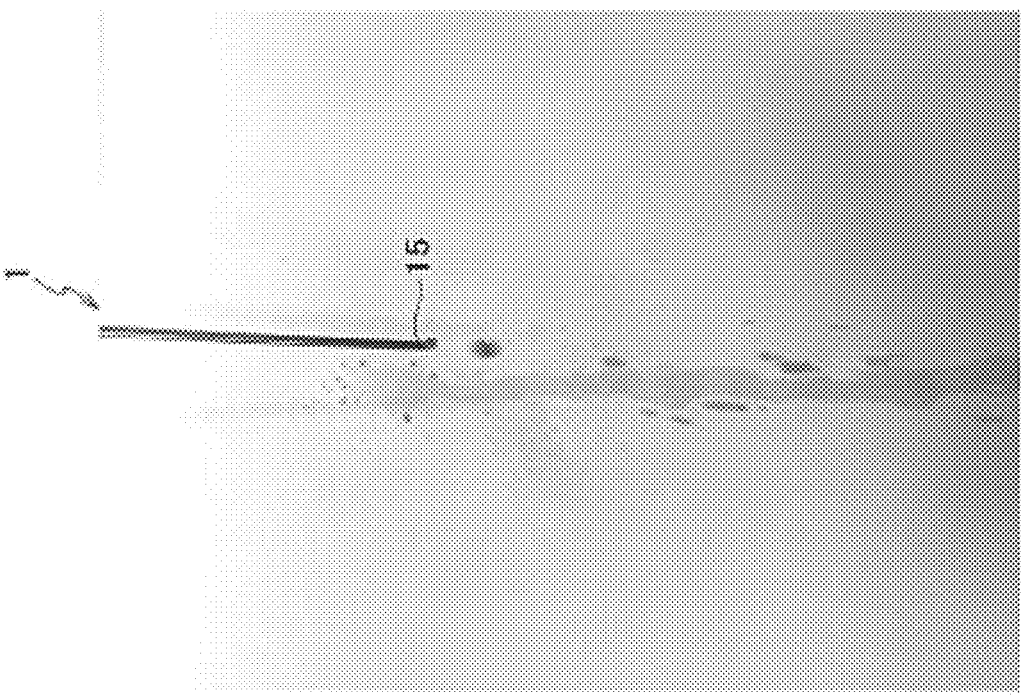
[Figure 6]

[Figure 7]
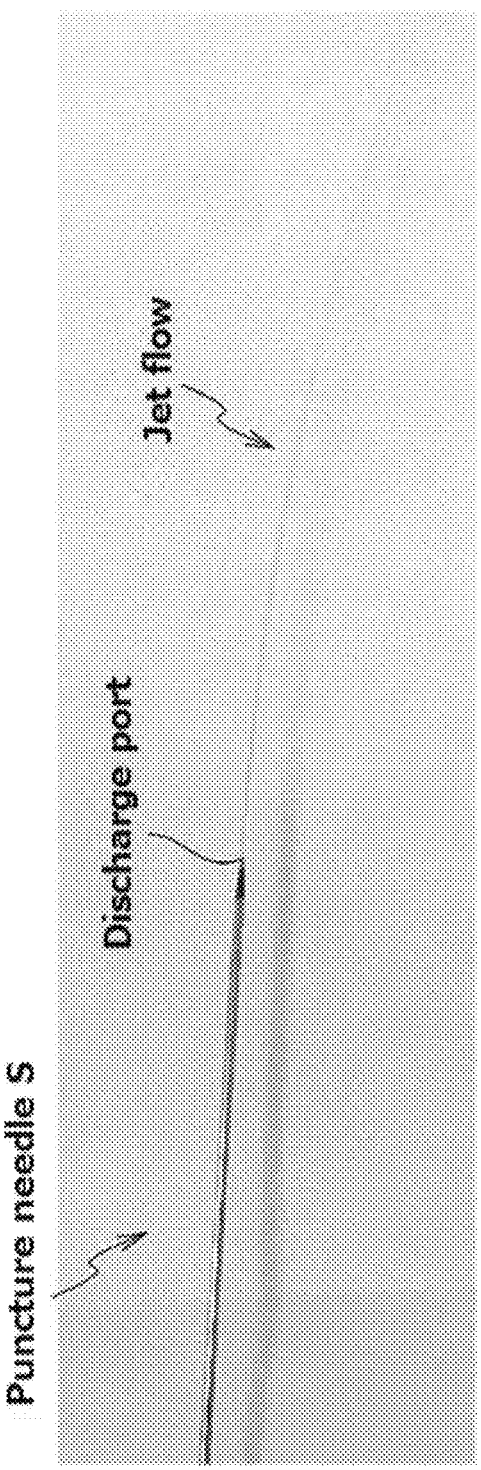

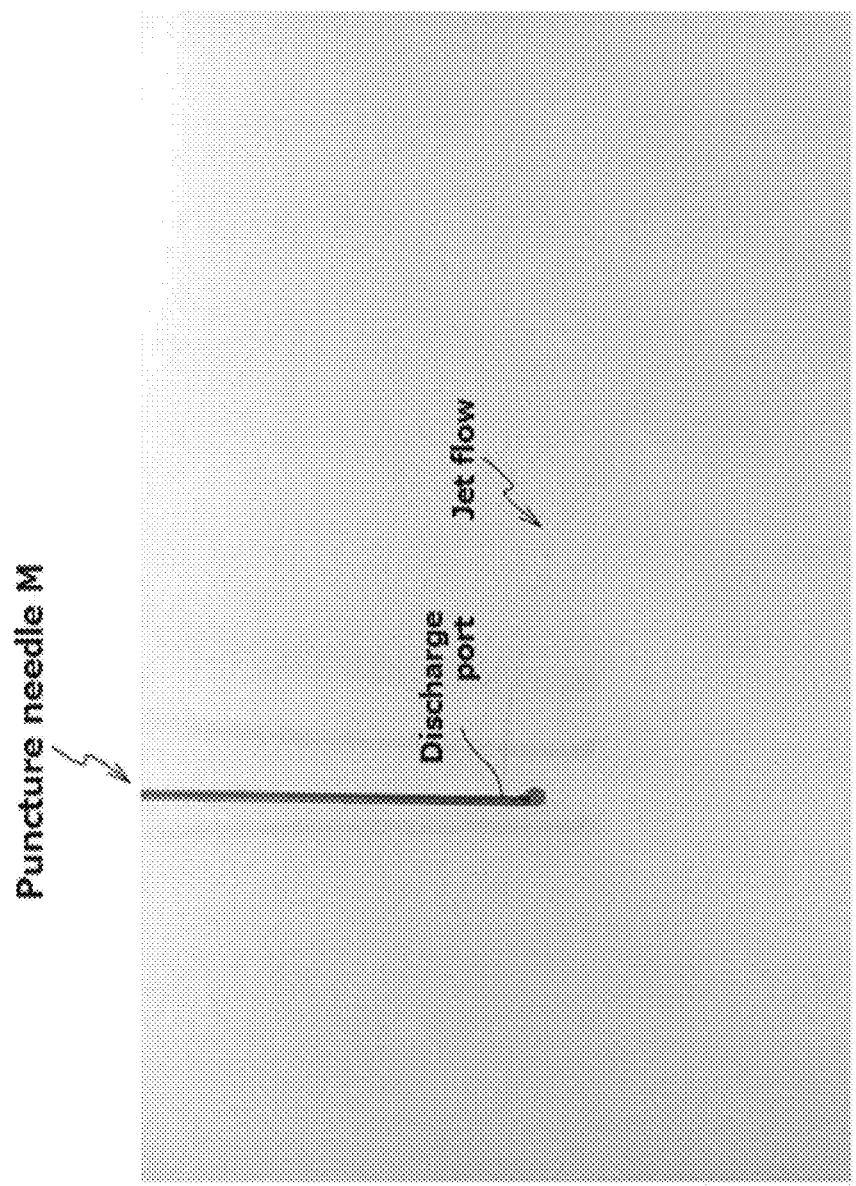
[Figure 8]

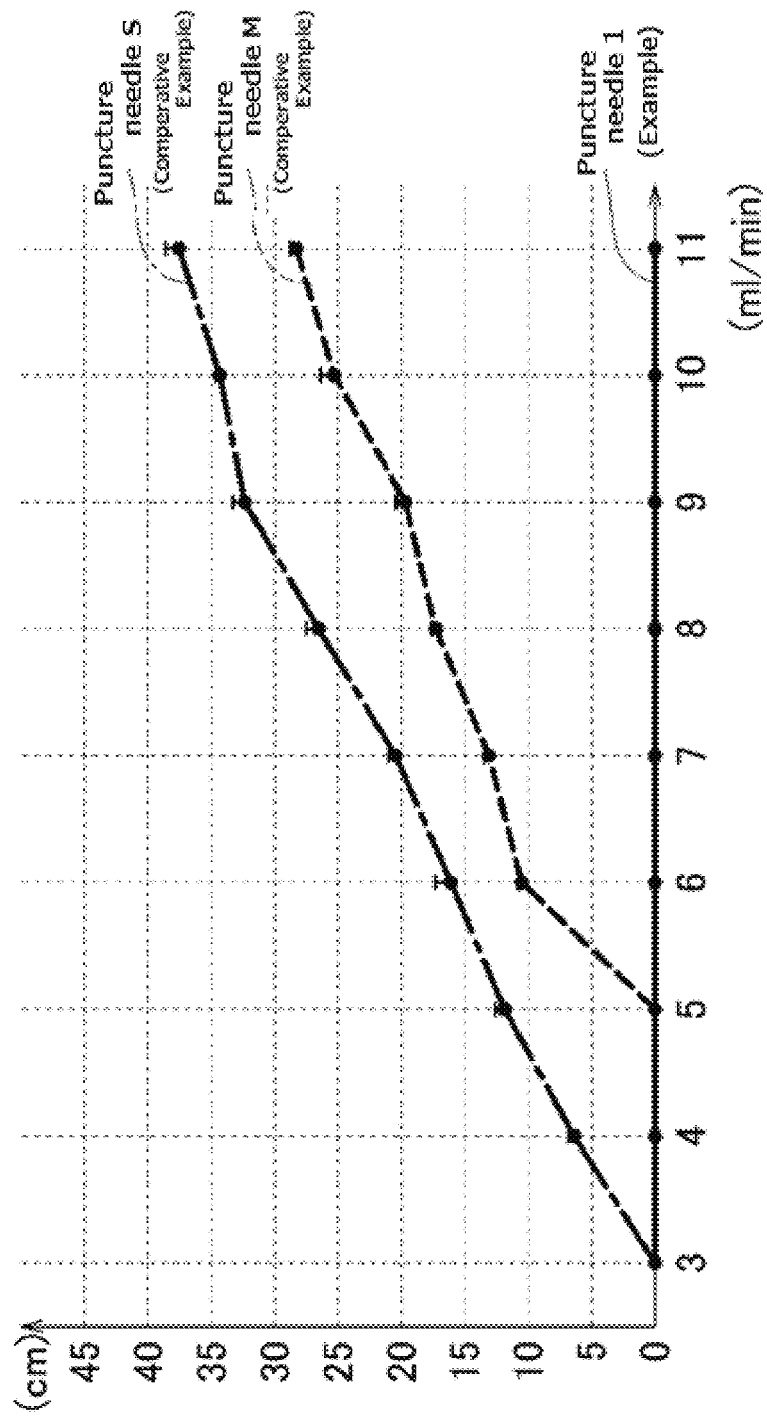
[Figure 9]

[Figure 10]
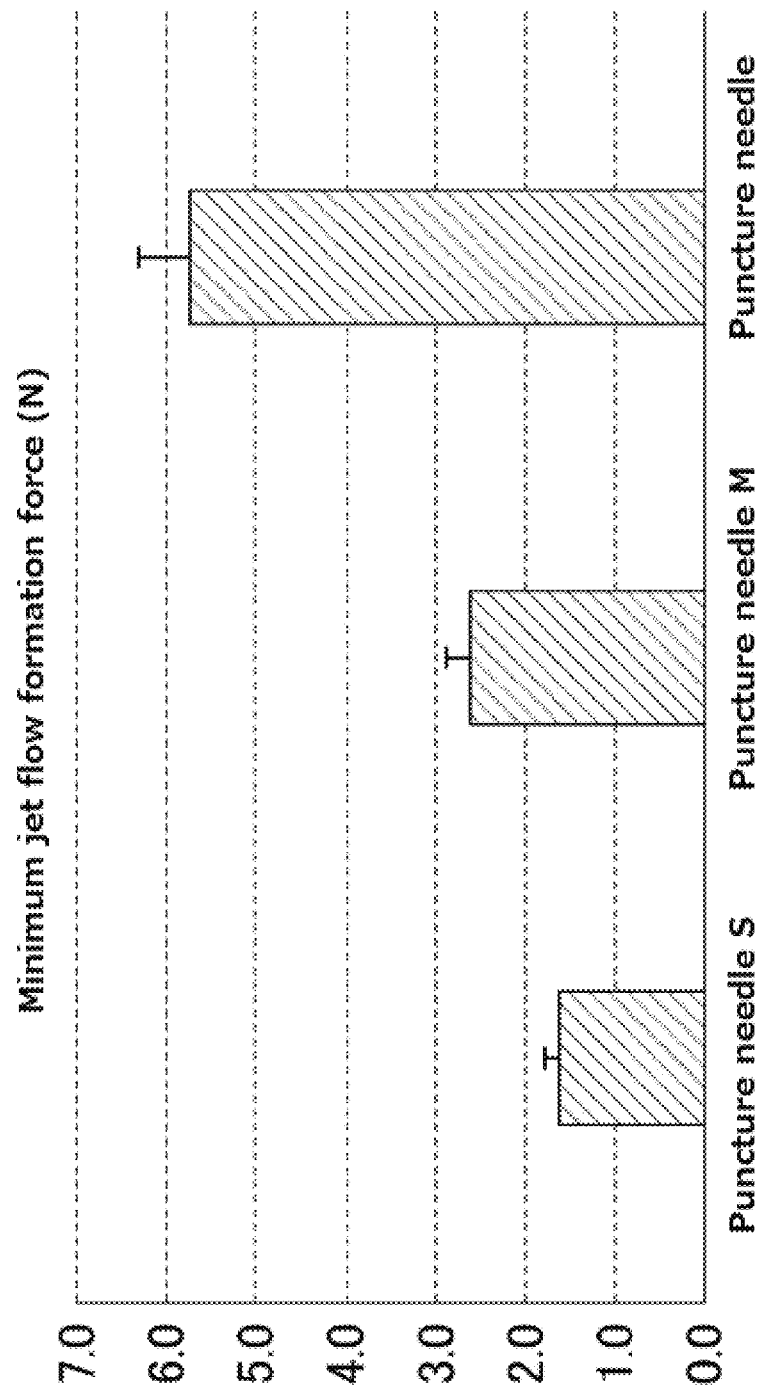

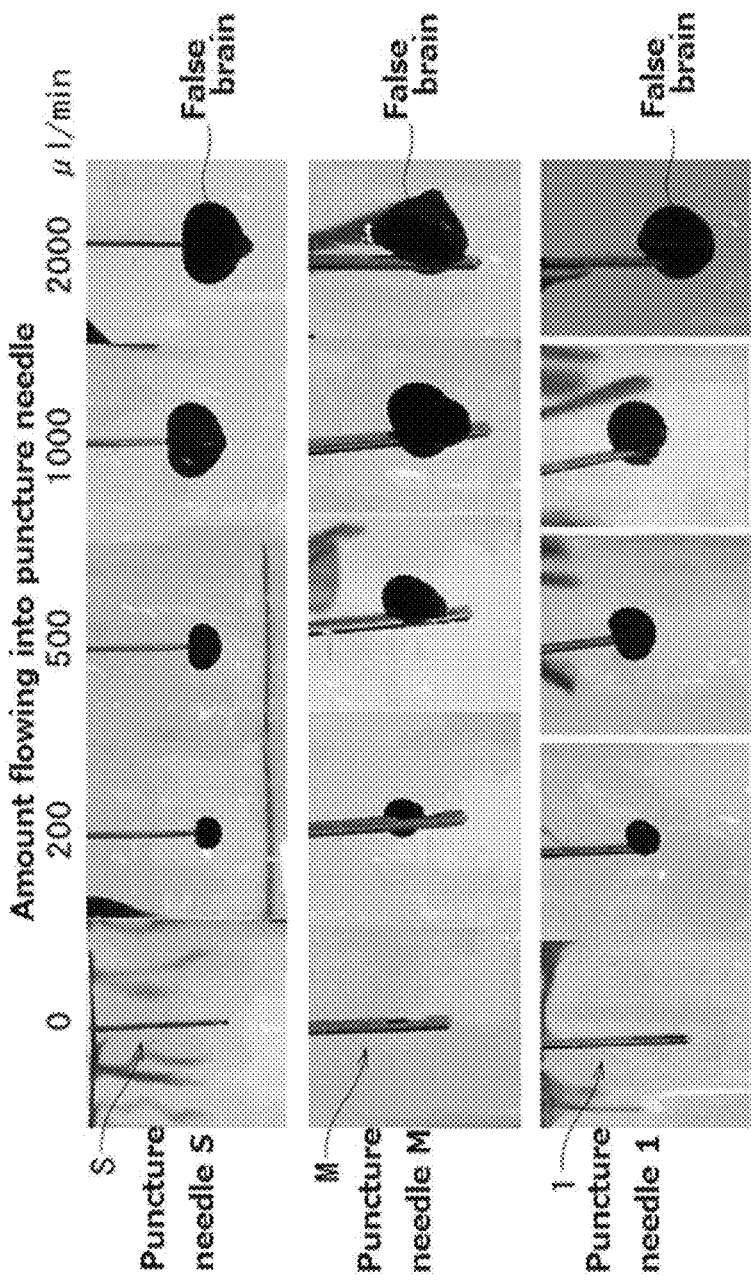
[Figure 11]

[Figure 12]
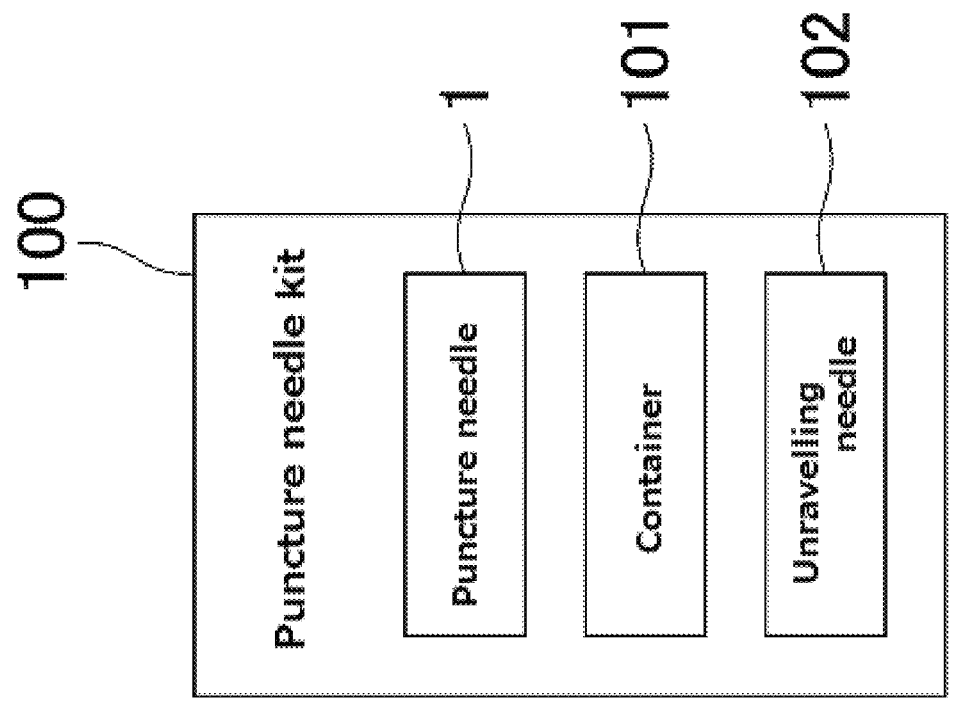

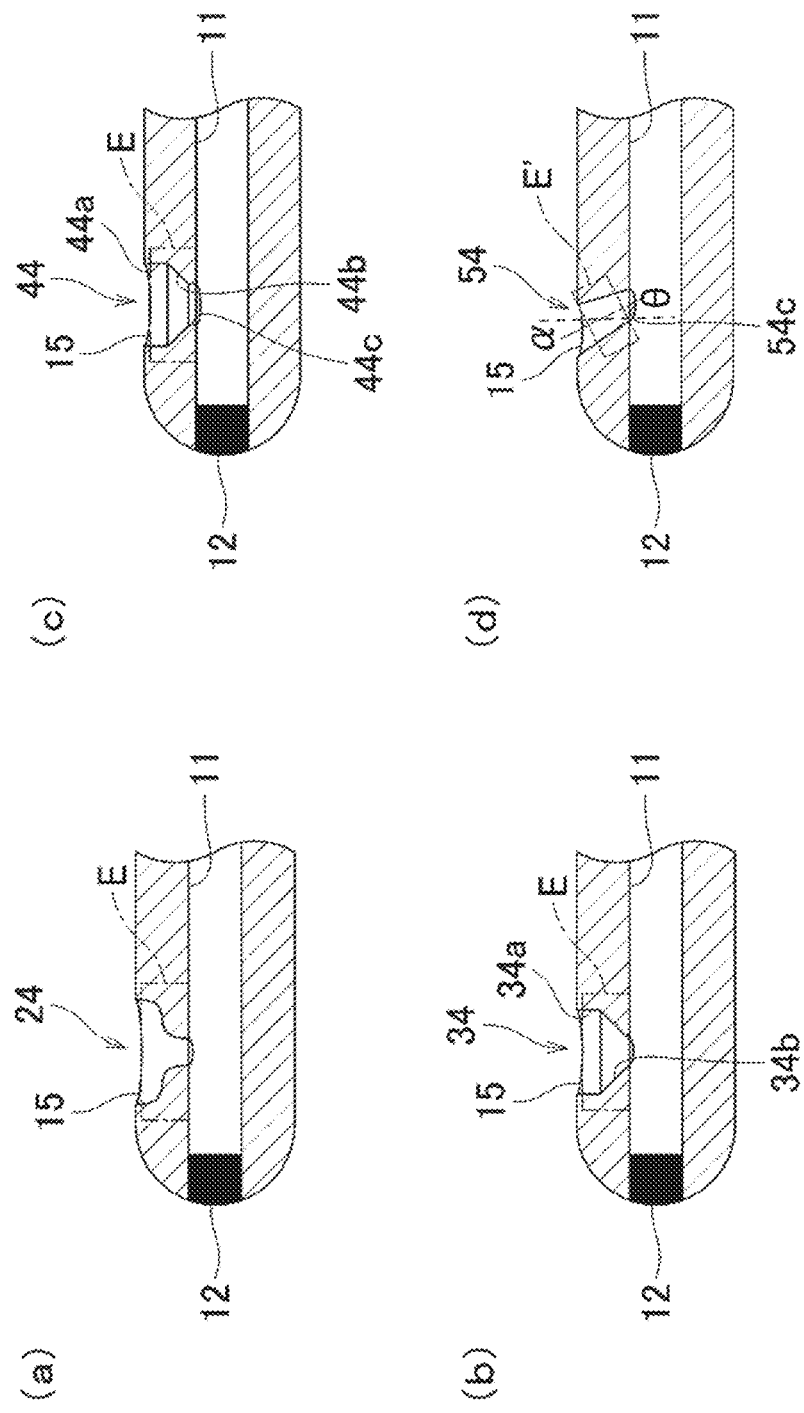
[Figure 13]

PUNCTURE NEEDLE, PUNCTURE NEEDLE KIT, AND STEREOTACTIC BRAIN SURGERY DEVICE

This application is a national phase of International Application No. PCT/JP2020/021373 filed 29 May 2020, which claims priority to Japan Application No. 2019-102123 filed 31 May 2019, and International Application No. PCT/JP2019/047526 filed 4 Dec. 2019, the entireties of which are hereby incorporated by reference.

TECHNICAL FIELD

The present disclosure relates to a puncture needle, and puncture needle kit, particularly for a living organism, and stereotactic brain surgery device.

BACKGROUND ART

One example of a puncture needle for infusing an object with fluidity such as liquid into a brain or spinal cord (central nervous system) is the needle device of Patent Literature 1. The needle device of Patent Literature 1 is used by being inserted in a brain from a front end part. A syringe in which liquid is stored is connected at a back end part of the needle device. A window part (discharge path) for infusion of liquid is formed at the front end part of the needle device, wherein the liquid is discharged from an aperture (discharge port) of the window part into the brain by manipulating the syringe.

CITATION LIST

Patent Literature

[PTL 1] Patent Literature 1: Japanese Patent No. 5665027

SUMMARY OF INVENTION

Solution to Problem

The present invention provides the following items.
(Item 1)
A puncture needle for infusing an object with fluidity into a brain, comprising:
a needle body along a forward/backward direction, wherein a passage for the object is formed inside; and
a discharge port of the object formed at an outer surface of a front end part of the needle body,
  characterized in that:
  the needle body is a single tube comprising the passage; and
  a surface area of a cross section of the discharge path orthogonal to a direction in which the discharge path extends is increased smoothly toward the discharge port in at least one part of the discharge path and, in each position regarding an extending direction of the discharge path, is equal to or greater than a surface area of the cross section in a position closer to the passage.
(Item 2)
The puncture needle of item 1, wherein the puncture needle consists of stainless, metal such as aluminum, ceramic, or inflexible rigid resin.
(Item 3)
The puncture needle of item 1 or 2, wherein the puncture needle comprises a connection part in which a syringe is connected to a back end of a needle body, wherein a distance between a tip of the connection part and a tip of a needle body part is about 170 mm to about 220 mm, wherein the needle body has an outer diameter that is about 1.6 mm or less.
(Item 4)
The puncture needle of any one of items 1 to 3, characterized in that an outer surface of the front end part comprises: a front end surface anteriorly projecting while smoothly bending; and a cylindrical side surface connected with the front end surface.
(Item 5)
The puncture needle of item 4, characterized in that a front end of the discharge port is positioned posterior to a front end of the passage and is positioned at a boundary between the front end surface and the side surface or positioned posterior to the boundary.
(Item 6)
The puncture needle of item 4 or 5, characterized in that the discharge port is formed behind the front end surface.
(Item 7)
The puncture needle of any one of items 1 to 6, characterized in that:
  the front end part has a cylindrical side surface; and
  at least one part of the discharge port is formed on the side surface.
(Item 8)
The puncture needle of any one of items 1 to 7, characterized in that an outer surface of the needle body is a surface contacting an organism upon puncturing, wherein a wall part from a passage of the needle body to an outer surface consists of a single layer.
(Item 9)
The puncture needle of any one of items 1 to 8, wherein the discharge path comprises a columnar part linked to the passage and a frustoconical part connecting the discharge port and the columnar part,
wherein an inner diameter of the passage is about 0.3 mm to about 1.2 mm, an inner diameter of the columnar part is about 0.3 mm to about 1.2 mm, and a frustoconical angle of the frustoconical part is about 90°.
(Item 10)
The puncture needle of item 9, wherein the discharge path further comprises a second columnar part between the discharge port and the frustoconical part,
wherein an inner diameter of the discharge port and a maximum inner diameter of the frustoconical part are about 1.2 mm to about 1.6 mm.
(Item 11)
The puncture needle of any one of items 1 to 7, wherein the discharge path comprises between the passage and the discharge port, from the passage side towards the discharge port, a frustoconical part or a columnar part with a first size and a frustoconical part or a columnar part with a second size that is greater than a first size,
wherein the first size is about 0.3 mm to about 1.2 mm and the second size is about 1.2 mm to about 1.66 mm.
(Item 12)
The puncture needle of items 1 to 7, wherein the discharge path comprises a frustoconical part linked to the passage and a columnar part provided between the discharge port and the frustoconical part,
wherein an inner diameter of the columnar part is about 0.3 mm to about 1.2 mm and a maximum inner diameter of the frustoconical part and the discharge port is about 1.2 mm to 1.6 mm.
(Item 13)
The puncture needle of any one of items 1 to 7, wherein the discharge path is provided with an angle α in the range that is over about 0° and about 30° in an inclined manner so that the discharge port side is positioned anterior to the passage side, wherein an inner diameter on the passage side is about 0.3 mm to about 1.2 mm and a size of the discharge port is about 0.5 mm to about 1.2 mm.

(Item 14)

The puncture needle of any one of items 1 to 13, characterized in that, when water is flowed into the passage from a syringe, an infusion pressure of the water suppresses generation of a jet flow up to about 5 N.

(Item 15)

The puncture needle of any one of items 1 to 14, characterized in that the object comprises a cell.

(Item 16)

A puncture needle kit, characterized by comprising:
a container storing the object; and
the puncture needle of item 15.

(Item 17)

The puncture needle kit of item 16, further comprising an unravelling needle.

(Item 18)

A cell preparation, characterized by comprising:
a container storing the object; and
the puncture needle of item 15.

(Item 19)

A stereotactic brain surgery device, comprising:
the puncture needle of item 15;
a fixing frame fixed to a head part;
a head pin for fixing the fixing frame to the head part;
an arc-like frame that can be fixed to the fixing frame; and
a stopper that can be fixed to any position on the arc-like frame and defines an insertion length of the puncture needle.

(Item 20)

A method of administering a cell into a brain, the method comprising:
A) the step of providing a container for storing an object;
B) the step of disposing liquid comprising a cell in the container for storing the object;
C) the step of mounting the puncture needle of any one of items 1 to 14 on the container;
D) the step of filling the liquid comprising the cell to a tip so as to remove air inside as needed;
E) the step of advancing the puncture needle to a stopper in accordance with an angle of a stereotactic brain surgery device that was set beforehand while rotating a needle as needed; and
F) the step of administering the cell upon touching the stopper.

Furthermore, the present invention provides the following items.

(Item 1)

A puncture needle for infusing an object with fluidity into a central nervous system, comprising:
a needle body along a forward/backward direction, wherein a passage for the object is formed inside;
a discharge port of the object formed at an outer surface of a front end part of the needle body; and
a discharge path for the object extending from the passage to the discharge port,
characterized in that a surface area of a cross section of the discharge path orthogonal to a direction in which the discharge path extends is increased smoothly towards the discharge port in at least one part of the discharge path and, in each position regarding an extending direction of the discharge path, is equal to or greater than a surface area of the cross section in a position closer to the passage.

(Item 2)

The puncture needle of item 1, characterized in that an outer surface of the front end part comprises: a front end surface anteriorly projecting while smoothly bending; and a cylindrical side surface connected with the front end surface.

(Item 3)

The puncture needle of item 2, characterized in that a front end of the discharge port is positioned posterior to a front end of the passage and is positioned at a boundary between the front end surface and the side surface or positioned anterior to the boundary.

(Item 4)

The puncture needle of item 2 or 3, characterized in that the discharge port is formed behind the front end surface.

(Item 5)

The puncture needle of item 1 or 2, characterized in that:
the front end part has a cylindrical side surface; and
at least one part of the discharge port is formed on the side surface.

(Item 6)

The puncture needle of any one of items 1 to 5, characterized in that
an outer surface of the needle body is a surface contacting an organism upon puncturing,
wherein a wall part from a passage of the needle body to an outer surface consists of a single layer.

(Item 7)

The puncture needle of any one of items 1 to 6, characterized in that, when water is flowed into the passage from a syringe, a minimal value of a force applied to a syringe so that water discharged from the discharge port would form a jet flow is 2.6 N or greater.

(Item 8)

The puncture needle of any one of items 1 to 7, characterized in that, when water is flowed into the passage from a syringe while applying any size of force that is less than 5.7 N to a syringe, water discharged from the discharge port does not form a jet flow.

(Item 9)

The puncture needle of any one of items 1 to 8, characterized in that the object comprises a cell.

(Item 10)

A puncture needle kit, characterized by comprising:
a container storing the object; and
the puncture needle of item 9.

In the present disclosure, in addition to the explicitly shown combination, the above-mentioned one or more feature is intended to be provided in further combination. Those skilled in the art would further recognize another embodiment and advantage of the present disclosure when those skilled in the art read and understand the following detailed explanation as needed.

Advantageous Effects

The inventors of the present invention were the first ones to recognize that a conventional puncture needle (e.g., Patent Literature 1) has the fear of forming a jet flow of liquid or the like discharged from a discharge port in accordance with the syringe manipulation situation (see FIG. 6 and FIG. 7 of the present application) and has the risk of the formed jet flow causing injury to a central nervous system, and the inventors of the present invention found out that these risks would be reduced by the present disclosure. In addition, the inventors of the present invention were the first ones to recognize that the conventional puncture needle represented by Patent Literature 1 is a double pipe consisting of an outer needle and an inner needle, which causes the pore for insertion to a brain or central nervous system of a spinal cord to be large, the burden for opening a pore to the central nervous system to be great and the risk of causing injury to the central nervous system to be high, and the inventors of the present invention found out that these risks would be reduced by the present disclosure.

BRIEF DESCRIPTION OF DRAWINGS

FIG. 1 is a front view of the puncture needle of the first embodiment which is one exemplary embodiment of the present disclosure.

FIG. 2 is a partially enlarged view of FIG. 1 including a partial cross section of the puncture needle.

FIG. 3(a) is a partially enlarged view of FIG. 2. FIG. 3(b) is a plane view of FIG. 3(a).

FIG. 4 is a schematic view of a stereotactic brain surgery device comprising the puncture needle of FIG. 1.

FIG. 5 is a diagram showing a state in which a stereotactic brain surgery device is mounted on the cranium of a patient.

FIG. 6 is a photograph showing an experimentation result using one Example of the puncture needle of FIG. 1.

FIG. 7 is a photograph showing an experimentation result using Conventional Example 1 with respect to the Example of FIG. 6.

FIG. 8 is a photograph showing an experimentation result using Conventional Example 2 with respect to the Example of FIG. 6.

FIG. 9 is a graph showing experimentation results including the results of FIG. 6 to FIG. 8.

FIG. 10 is a graph showing experimentation results that are different from FIG. 6 to FIG. 9.

FIG. 11 is a photograph showing further different experimentation results.

FIG. 12 is an outline diagram showing the configuration of the puncture needle kit of the second embodiment which is a different embodiment of the present disclosure.

FIG. 13 is a cross-sectional view of a front end part of the puncture needle of other modified examples.

DESCRIPTION OF EMBODIMENTS

The present disclosure is explained hereinafter. Throughout the entire specification, a singular expression should be understood as encompassing the concept thereof in the plural form, unless specifically noted otherwise. Thus, singular articles (e.g., "a", "an", "the", and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present disclosure pertains. In case of a contradiction, the present specification (including the definitions) takes precedence. The terms used in the present disclosure and the general technique are explained.

As used herein, "about" means ±10% of the numerical value that follows.

As used herein, "object with fluidity" refers to a matter with fluidity such as gas or liquid, or a configuration product or the like which is configured with a combination of matters with fluidity like a cell or the like, which is exemplified by a liquid agent, cell or the like. A matter that can be infused with an injector is normally within the scope of the object with fluidity.

The present disclosure generally provides a puncture needle, puncture needle kit and stereotactic brain surgery device, in which an object such as liquid discharged from a discharge port is less liable to form a jet flow, and less liable to cause injury to the central nervous system. In one example, the present disclosure provides a puncture needle for infusing an object with fluidity into a brain. This puncture needle comprises a needle body along a forward/backward direction, wherein a passage for the object is formed inside, and a discharge port of the object formed at an outer surface of a front end part of the needle body, wherein the needle body is a single tube comprising the passage, wherein a surface area of a cross section of the discharge path orthogonal to a direction in which the discharge path extends is increased smoothly towards the discharge port in at least one part of the discharge path and, in each position regarding the extending direction of the discharge path, is equal to or greater than a surface area of the cross section in a position closer to the passage.

In one non-limiting embodiment, according to the puncture needle of the present disclosure, the surface area of the cross section of the discharge path is increased smoothly towards the discharge port in at least one part of the discharge path. That is, at least one part of the discharge path is widened towards the discharge port. In addition, in each position regarding the extending direction of the discharge path, the surface area of the cross section of the discharge path is equal to or greater than a surface area of a cross section in a position closer to the passage. In other words, the surface area of the cross section of the discharge path does not change so as to be smaller towards the discharge port. This causes the object discharged from the discharge port to be less liable to form a jet flow (e.g., see FIG. 6 of the present application). In addition, since the needle body is a single tube that comprises a passage for an object, the needle body can have a smaller outer diameter for the tube compared to a conventional double tube, thereby reducing the burden against the brain or central nervous system (see, for example, FIG. 2 of the present application). The outer diameter of the needle tube may be any outer diameter. For example, the outer diameter of the needle body is about 2.0 mm or less, preferably about 1.6 mm or less, more preferably about 1.2 mm or less. Therefore, a puncture needle that is less liable to cause injury to the central nervous system is realized.

In another non-limiting embodiment, the inventors of the present invention thought that since a jet flow is formed in a conventional puncture needle because a discharge path is linearly formed (see FIG. 6 of Patent Literature 1), i.e., because the surface area of the cross section of the discharge path is constant. Although not wishing to be bound by any theory, the puncture needle of the present disclosure, which is for infusing an object with fluidity into a central nervous system, can unexpectedly suppress or lose a jet flow by the surface area of the discharge path orthogonal to the direction in which the discharge path extends increasing smoothly towards the discharge port in at least one part of the discharge path and, in each position regarding the extending direction of the discharge path, being equal to or greater than a surface area of a cross section in a position closer to the passage. In the puncture needle of the present disclosure comprising a needle body along a forward/backward direction, wherein a passage for an object is formed inside, a discharge port of the object formed at an outer surface of a front end part of the needle body and a discharge path of the object extending from the passage to the discharge port, this effect is also enhanced by the needle body being a single tube comprising a passage for an object.

In another non-limiting embodiment, it is preferable in the present disclosure that an outer surface of the front end part comprises a front end surface anteriorly projecting while smoothly bending and a cylindrical side surface connected to the front end surface. A conventional puncture needle has a sharply formed front end, or has a flatly formed front end as in Patent Literature 1. When such a puncture needle is inserted into an organism, the risk of the needle causing injury to a tissue such as a blood vessel would be high. In this regard, according to the above-mentioned configuration, the front end surface is curved, thereby reducing the fear of the needle causing injury to a tissue upon insertion into an organism.

In another non-limiting embodiment, it is preferable in the present disclosure that a front end of the discharge port is positioned posterior to a front end of the passage and positioned at a boundary between the front end surface and the side surface or positioned anterior to the boundary. There is a case of a cell or liquid being wasted by being accumulated in a portion anterior to a discharge port in a passage within a needle body. In this regard, according to the above-mentioned configuration, the front end of the discharge port is disposed at a boundary between the front end surface and the side surface or anterior to that. Therefore, in a passage, the portion from the front end thereof to the discharge path is liable to be relatively short. Thus, the amount of cell or liquid wasted by being accumulated in the portion from the front end to the discharge path of the passage would be relatively small.

In another non-limiting embodiment, it is preferable in the present disclosure that the discharge port is formed behind the front end surface. According to the above, the discharge port would be hidden behind the front end surface when seen from the anterior. Therefore, a tissue within an organism is less liable to intrude into the discharge port upon anteriorly inserting a puncture needle into the organism.

In another non-limiting embodiment, it is preferable in the present disclosure that the front end part has a cylindrical side surface and at least one part of the discharge port is formed at the side surface. According to the above, since at least one part of the discharge port is formed at the side surface, a tissue within an organism is less liable to intrude into the discharge port upon insertion of a puncture needle.

In another non-limiting embodiment, it is preferable in the present disclosure that an outer surface of the needle body is a surface contacting an organism upon puncturing and a wall part from a passage to the outer surface of the needle body consists of a single layer. According to the above, the inner diameter of the passage is liable to be formed as great as possible while suppressing the outer diameter of the needle body. The greater the inner diameter of a passage becomes, the less liable for a cell or the like to be clogged inside. Thus, it is effective that the inner diameter of the passage can be easily made as great as possible in the point that it is possible to prevent a cell or the like from being clogged inside the passage.

In another non-limiting embodiment, it is preferable in the present disclosure that, when water is flowed into the passage from the syringe, the minimum value of force applied to a syringe so that the water discharged from the discharge port will form a jet flow is about 1.5 N or greater, about 2.0 N or greater, about 2.3 N or greater, about 2.6 N or greater, or about 3.0 N or greater. According to the above, a puncture needle that is less liable to form a jet flow compared to a conventional puncture needle is realized. In this case, the maximum value of force applied to the syringe so that water discharged from the discharge port will form a jet flow may be about 6.0 N, about 5.7 N, about 5.4 N, about 5.0 N.

In another non-limiting embodiment, the object may comprise a cell in the present disclosure. When a call is comprised in an object, when a cell is clogged within a puncture needle, there is a fear of a user applying large pressure to the puncture needle in order to overcome the clogging. In view of the above, the fear of an object that flows out from a discharge port forming a jet flow would increase. Therefore, the technical significance of applying the technique provided in the present disclosure in such a case is great.

In another aspect, the present disclosure provides a method of administering a cell to a brain. This administration method comprises: A) the step of providing a container for storing an object; B) the step of disposing liquid (e.g., suitable liquid such as saline) comprising a cell (e.g., cells comprising a stem cell for brain infarction) in the container for storing the object; C) the step of mounting any puncture needle of the present disclosure on the container; D) the step of filling the liquid comprising the cell to a tip so as to remove air inside as needed (when air is removed, this step is not particularly necessary); E) the step of advancing the puncture needle to a stopper in accordance with an angle of a stereotactic brain surgery device that was set beforehand while rotating a needle as needed; and F) the step of administering the cell upon touching the stopper. Injury of a tissue inside the brain can be minimized by rotating the needle.

In this regard, a stereotactic brain surgery device may comprise: a fixing frame fixed to a head part; a head pin for fixing the fixing frame to the head part; an arc-like frame that can be fixed to the fixing frame; and a stopper that can be fixed to any position on the arc-like frame and defines an insertion length of the puncture needle.

When a needle is advanced to a stopper in accordance with an angle of a stereotactic brain surgery device such as a Leksell frame that was set beforehand, it will be confirmed that a guide stop is at a suitable position (e.g., may be 0 mm, may be −7 mm, or may be any other positions). Upon advancing a needle, the needle is advanced while rotating the needle so as not to cause injury to a brain blood vessel. That is, after wetting the tip, the needle is advanced while slowly rotating the needle for five minutes or longer. In this regard, the suitable position can be suitably changed depending on the position of the hole. For example, when a needle to be used has a hole from which a cell exits that is present at a place that is 7 mm from the tip of the needle, while a cell can be administered at a periphery of a target when punctured at ±0 mm, a brain tissue would be pierced 7 mm deeper than planned. Thus, it can be considered that a cell can fill the space where the needle has passed by pulling out the needle, and it is possible to achieve an actual site where the cell reaches even when the location where the cell exits still has 7 mm to reach the intended target. When a needle to be used is provided with a fan-shaped hole where a cell exists substantially near the tip, it is possible to employ, but not limited to, ±0 mm.

When a target location is reached and a stopper is touched, a cell is administered, and a syringe with a cell inside (e.g., 1 ml size) is attached to be slowly (e.g., for five minutes or longer) administered (as one example, a high dose is fifty million cells/1000 μl). The needle is pulled (e.g., about 3 mm) out to the front (in the case of −7 mm, it would be −10 mm) at the point when an appropriate amount (e.g., 200 μl) is in. This causes the cell to remain centering around a cavity where the needle was pierced. Herein, a small amount (e.g., 200 μl) can be administered again. A dead cavity of a needle (normally, but not limited to, about 20 μl) is within the scope of a margin of error. Then, the needle is left to stand at this location for an appropriate amount of time (e.g., five minutes), and then the needle can be pulled out.

Next, an appropriate hemostatic agent (e.g., gelfoam (medical gelfoam, sterile absorbable gelatin preparation which is a hemostatic agent; obtainable from Pfizer or the like), fibrin glue (Bolheal® that can be obtained from Teijin, periplast that can be obtained from CSL Behring) and the like) are placed at the surface of the hole, wherein flow-out of a cell can be prevented. This functions so that the pressure would not cause flowback of a cell that was deeply put in from the punctured hole upon pulling out the needle. In addition, the dura mater is filled with a hemostatic agent (e.g., gelfoam or the like). Herein, a tool such as a Burr hole cap is not used to decrease an infection risk. This causes the opened hole to be substituted with gelfoam, which would be replaced with a fibroblast in the future.

In another non-limiting embodiment, a puncture needle kit based on another viewpoint of the present disclosure comprises a container storing the object and the puncture needle. According to the above, the treatment of infusing an object taken out from a container into a central nervous system can be practiced using the puncture needle of the present disclosure.

Preferable specific embodiments of the present disclosure are explained below. The specific embodiments provided below are provided for better understanding of the present disclosure, wherein it is understood that the scope of the present disclosure should not be limited to the description below. Therefore, it is clear that those skilled in the art can appropriately make modifications within the scope of the present disclosure while considering the description herein. In addition, it is understood that the following embodiments of the present disclosure can be used alone or can be used in combination.

First Embodiment

A puncture needle 1 of the first embodiment which is one embodiment of the present disclosure is explained below while referring to FIG. 1 to FIG. 3. The puncture needle 1 is used for transplanting a cell such as a stem cell to a specific position of a brain in surgery using a stereotactic brain surgery device for treating brain infarction. The puncture needle 1 comprises a needle body 10 linearly extending along one direction and a connection part 20 where a syringe to be fixed is connected to a back end part of the needle body as shown in FIG. 1. A cell to be administered into an organism is supplied from the syringe to the puncture needle 1. Furthermore, the type and material quality of the connected syringe may be any type and material quality. Furthermore, it is preferable that the connection part 20 is configured so as to enable connection of a Hamilton syringe. According to the above, it is possible for a small amount of cells or liquid to precisely flow into the puncture needle 1.

In addition, the stereotactic brain surgery device to which the puncture needle 1 is attached may be in any form. For example, may be a Komai-style stereotactic brain surgery device, or may be a Leksell frame.

Hereafter, the direction along the needle body 10 is referred to as the forward/backward direction as shown in FIG. 1 to FIG. 3. Anterior is a direction in which the puncture needle 1 is inserted into an organism and posterior is a direction opposite thereto. In addition, the one direction orthogonal to the forward/backward direction is referred to as the upward/downward direction as shown in FIG. 1, FIG. 2 and FIG. 3(a). A syringe insertion hole 21 where the tip of the syringe is inserted and a body insertion pore 22 where the needle body 10 is inserted are formed inside the connection part 20 as shown in FIG. 2.

The needle body 10 is a circular cylindrical member consisting of stainless, metal such as aluminum, ceramic, or inflexible rigid resin (with less flexibility). In the present disclosure, a circular shape does not strictly need to be a circle, but is enough if it is a medically allowed shape, which may be substantially circular (e.g., elliptical, or the like). It is possible to accurately insert a puncture needle to a desired therapy target point by making the material quality of the needle body 10 inflexible with metal, rigid resin, or the like. Preferably, a needle body is made of stainless that enables preparation such as sterilization processing at low cost. A passage 11 for a cell to pass through is formed inside the needle body 10 as shown in FIG. 2 and FIG. 3(a). The passage 11 is defined by an inner surface of a penetration port where the needle body is penetrated in the forward/backward direction and a surface of an occlusion part 12 made of metal wherein the aperture part of the front end of this penetration port is occluded. The passage 11 is opened towards the posterior in the back end of the needle body 10 and in communication with the syringe insertion hole 21 of the connection part 20. A cell supplied from a syringe is infused into the passage 11 via the syringe insertion hole 21. The cell infused into the passage 11 goes through the passage 11 by being pressured in from a syringe and towards a front end part 13 of the needle body 10. The needle body 10 is not a conventional double tube but consists of a single tube in the present embodiment. That is, the puncture needle 1 is different from the needle of Patent Literature 1 having a double tube structure of an inner needle and an outer needle. Therefore, the outer diameter of the needle body 10 can be suppressed, and load to a patient or injury to the central nervous system can be reduced thereby. In addition, in the present embodiment, the needle body 10 consists of a single layer, wherein the wall part from the passage 11 to the outer surface is not divided in the middle. By carrying out the above, the inner diameter of the passage 11 can be formed as great as possible. In addition, the greater the inner diameter of the passage 11, the less liable for a cell to be clogged inside. When a cell is clogged inside the passage 11, there is a higher fear of injuring the inside of a brain by a cell and liquid discharged from a discharge port 15 forming a jet flow as discussed above. Therefore, as discussed above, the fact that the inner diameter of the passage 11 made of a single layer can easily be made as great as possible while suppressing the size of the outer diameter of the needle body made of a single tube is effective from the viewpoint of avoiding formation of a jet flow.

The inner diameter of the passage 11 may be any diameter. For example, the inner diameter is about 0.3 mm to about 1.2 mm, preferably about 0.5 mm to about 1.2 mm.

The length of the puncture needle may be any length. For example, the distance between a tip 20a of the connection part 20 and a tip 10a of the needle body 10 is about 150 mm to 230 mm, preferably about 170 mm to about 220 mm, more preferably about 170 mm to about 200 mm.

The front end part 13 of the needle body 10 has a front end surface 13a which is an outer surface anteriorly projecting and a side surface 13b which is a cylindrical outer surface as shown in FIG. 3(a) and FIG. 3(b). The front end surface 13a has a smoothly bent hemispherical shape, and is smoothly connected with the side surface 13b at the back end.

A discharge port 15 that is circular when seen from above is formed in the front end part 13 as shown in FIG. 3(b). A cell supplied from a syringe into the passage 11 is discharged from the discharge port 15. The front end 15a of the discharge port 15 is positioned exactly at a boundary B between the front end surface 13a and the side surface 13b. That is, the entirety of the discharge port 15 is formed within the range of the side surface 13b and the discharge port 15 would be disposed behind the front end surface 13a. Therefore, the discharge port 15 will not be able to be seen as being hidden behind the front end surface 13a when the puncture needle 1 is seen from the anterior.

A discharge path 14 for a cell upwardly extending from the passage 11 to the discharge port 15 is formed inside the front end part 13. The discharge path 14 consists of a substantially frustrum-like frustoconical part 14a and a substantially column-like columnar part 14b. The lower end of the columnar part 14b is connected with the passage 11. The connection position of the columnar part 14b and the passage 11 is a position that is posteriorly spaced apart from the front end of the passage 11. The upper end of the columnar part 14b is connected with the lower end of the frustoconical part 14a. The lower end of the frustoconical part 14a has the same shape as the upper end of the columnar part 14b, i.e., a circular inner diameter with the same size as the inner diameter of the columnar part 14b. The upper end of the frustoconical part 14a is connected with the discharge port 15 of a cell that is opened at the side surface 13b of the front end part 13.

The discharge path 14 is formed so that the cross section thereof would have the following characteristics. Unless specifically noted otherwise, a cross section of the discharge path 14 is a cross section orthogonal to the direction in which the discharge path 14 extends, i.e., a cross section orthogonal to the upward/downward direction of FIG. 3. In addition, a cross section of the discharge path 14 is defined within the range surrounded by the dashed line E of FIG. 3. The dashed line E corresponds to the range excluding the range where the discharge port 15 is formed and the range where an aperture 14c of the discharge path 14 to the passage 11 is formed. The frustoconical part 14a is formed so that the surface area of the cross section would smoothly become greater from the lower end towards the upper end. In addition, the surface area of the cross section is constant regarding the columnar part 14b. Thus, regarding the discharge path 14 consisting of the frustoconical part 14a and the columnar part 14b, a surface area of a cross section in any position regarding the upward/downward direction is also equal to or greater than a surface area of a cross section of a position closer to the passage 11 than said position. For example, a cross section of any position regarding the upward/downward direction in the frustoconical part 14a also has a surface area greater than a cross section of any position that is more on the passage 11 side than said cross section. In addition, a cross section of any position regarding the upward/downward direction in the columnar part 14b also has a surface area equal to a cross section of any position that is more on the passage 11 side than said cross section.

The use method of the puncture needle 1 is explained while referring to FIGS. 4 and 5. FIG. 4 is a schematic view of a stereotactic brain surgery device 200 comprising the puncture needle 1, and FIG. 5 is a diagram showing a state in which the stereotactic brain surgery device 200 is mounted on the cranium (head part) of a patient. A stereotactic brain surgery device 200 is set on the head part of a patient where a perforation has been formed at the cranium by trepanation as shown in FIGS. 4 and 5. The stereotactic brain surgery device 200 is a device for holding an insertion position and an insertion direction of a puncture needle 1 with respect to a brain at specific position and direction. The stereotactic brain surgery device 200 comprises a fixing frame 210, a head pin 211, an X-axis slide stand 220, a Y-axis slide stand 230, a Z-axis slide stand 240, an arc-like arm 250 and a puncture needle 1. The annular fixing frame 210 is made of metal and is mounted on the cranium of a patient. A plurality of head pins 211 are added to the fixing frame 210. The head pin 211 is for fixing the fixing frame 210 to the cranium and is configured to be movable towards inside the annular fixing frame 210. While the number of the head pints 211 may be any number, the number may be two, or may be three or more. In one embodiment, the number is four. The fixing frame 210 can be fixed to the cranium by mounting the fixing frame 210 on the cranium and moving the head pin 211 inside. In addition, the fixing frame 210 may comprise an X-axis slide stand 220 that is movable in a direction parallel to a surface of the fixing frame 210, a Y-axis slide stand 230 and a Z-axis slide stand 240 that is movable in a direction orthogonal to a surface of the fixing frame 210. An arc-like frame 250 is added to any of the X-axis to Z-axis slide stands 220, 230 and 240. The arc-like frame 250 is removably fixed to any of the X-axis to Z-axis slide stands 220, 230 and 240 by a fastening means such as a bolt. In the embodiment showed in the drawings, the stereotactic brain surgery device comprises all of the X-axis to Z-axis slide stands, but the present invention is not limited thereto. It is possible to choose to select or not to select as needed. This arc-like frame 250 is in a shape that forms one part on a spherical body surface centering around a therapy target point where the puncture needle 1 reaches. Therefore, the distance to the therapy target point is constant from any position of the arc-like frame 250. In addition, a puncture needle fixing part 260 that is movable on the arc-like frame 250 is added to the upper part of the arc-like frame 250. Furthermore, the puncture needle 1 would be inserted into the puncture needle fixing part 260. The puncture needle fixing part 260 comprises a base part that is movable on an arc-like frame 250 and an attachment part for attaching a puncture needle onto this base part. In addition, the puncture needle fixing part 260 is further provided with a stopper 261 for restraining the puncture needle 1 from entering deeper than a desired therapy target point (i.e., defining the insertion length of the puncture needle). The stopper 261 is configured to restrain insertion of the puncture needle 1 by engaging with the tip part 20a of the connection part 20 of the needle body 10. The stopper 261 may be provided to the puncture needle 1 itself and not the puncture needle fixing part 260.

Regarding the stereotactic 200 of the present disclosure, the puncture needle 1 is arbitrarily movable on the arc-like frame 250 and the arc-like frame 250 is movable in each direction by the X-axis slide stand 220, the Y-axis slide stand 230 and the Z-axis slide stand 240, thereby enabling the puncture needle 1 to reach a therapy target point from any point in the range covered by the fixing frame 210. Therefore, it is possible to reach a therapy target point from the entire range of the cranial surface.

The puncture needle 1 is inserted into a brain from a brain surface through a perforation using the stereotactic brain surgery device 200 of the present disclosure. Upon the insertion, the front end part 13 is directed in the insertion direction and the puncture needle 1 is inserted by being slid along the forward/backward direction. Preferably, upon inserting a puncture needle inside a brain, the puncture needle is inserted while being slightly rotated. By carrying out the above, the needle can be inserted so as not to cause injury to a brain blood vessel. Upon the insertion, the front end part 13 advances deep into the brain while the outer surface of the puncture needle 1 comprising the front end surface 13a and the side surface 13b contacts a tissue inside the brain. This causes the front end part 13 to reach a target point inside the brain. Next, a syringe storing a cell together with liquid such as saline is connected via a connection part at a back end part of the puncture needle 1. When an object stored in a syringe comprises cells, it is preferable that the cells be stored in the syringe after undergoing the operation of sufficient suspension to break a cell cluster. Next, the syringe is manipulated to pressure the inside cell and liquid into the puncture needle 1. This causes the cell and liquid to be discharged from the discharge port 15 of the puncture needle 1 into the brain through the passage 11 and the discharge path 14 inside the puncture needle 1. While a puncture needle was connected to a syringe after reaching a therapy target point in the explanation above, it is possible to have a puncture needle reach a therapy target point in a state in which the puncture needle is connected to a syringe.

According to the present embodiment explained above, the discharge path 14 of the puncture needle 1 has the following characteristics. First, in at least one part of the discharge path 14 (specifically, frustoconical part 14a), the surface area of the cross section thereof is increased smoothly towards the discharge port 15. That is, at least one part of the discharge path 14 widened towards the discharge port 15. Second, a surface area of a cross section of a discharge path 14 in any position regarding the direction in which the discharge path 14 extends is equal to or greater than a surface area of a cross section of a position closer to the passage 11 than said position. In other words, a surface area of a cross section of the discharge path 14 does not change so as to be smaller towards the discharge port 15. Meanwhile, if a cross section of the discharge path 14 is constant regardless of the position, or if the discharge path 14 is formed so that a cross section would be smaller (a cross section would narrow down) towards the discharge port 15 in anywhere in the middle of the discharge path 14, there is a fear of a cell and liquid discharged from the discharge port 15 forming a jet flow as shown in the Example discussed below. Specifically, in the case in which a cell is clogged inside the passage 11 or the like, there is a higher fear of forming a jet flow when there is a need for a greater pressure for pressuring in the cell in a syringe. Furthermore, when a cell and liquid discharged from a discharge port 15 form a jet flow, there is a higher fear of generating injury to the brain by the impact to the brain that is caused by the jet flow. In this regard, the discharge path 14 of the puncture needle 1 has the first and second characteristics as described above. Thus, as shown in the Example discussed below, the puncture needle 1 is less liable to form a jet flow. Therefore, a cell and liquid discharged from the discharge port 15 is less liable to cause injury to the brain.

In addition, in the present embodiment, the front end part 13 of the puncture needle 1 has a hemispherical front end surface 13a. Meanwhile, when a front end of a needle is sharply formed or a front end surface is flatly formed, there is a higher risk of the needle causing injury to a tissue such as a blood vessel upon inserting the needle into a brain. In this regard, since the front end surface 13a is curved, there is a lower fear of a needle causing injury to a tissue upon insertion into a brain.

In addition, in the present embodiment, the discharge port 15 for a cell is disposed within the range of the side surface 13b of the front end part 13. Therefore, the discharge port 15 will not be seen as being hidden behind the front end surface 13a when the needle body 10 is seen from the anterior. If the discharge port 15 is formed at the front end surface 13a and not the side surface 13b, the discharge port 15 would be opened towards the anterior. Thus, the possibility of a tissue of a brain intruding the discharge port 15 upon inserting the puncture needle 1 into the brain would increase. In this regard, since the discharge port 15 is disclosed within the range of the side surface 13b and is hidden behind the front end surface 13a as described above, there is lower fear of a tissue intruding into the discharge port 15.

In addition, in the present embodiment, the front end 15a of the discharge port 15 is positioned at a boundary B between the front end surface 13a and the side surface 13b. If the front end 15a of the discharge port 15 is disposed posterior to this position, the portion from the front end to the discharge path 14 would be longer in the passage 11. It is possible that a cell that reached this portion would remain in said portion without being discharged from the discharge port 15. Therefore, there is a fear of the amount of wasted cells being greater when this portion is long. In this regard, since the front end 15a of the discharge port 15 is positioned at the boundary B between the front end surface 13a and the side surface 13b as described above, the length of the portion from the front end of the passage 11 to the discharge path 14 would be relatively smaller. Therefore, since it is possible make the length for inserting a puncture needle into a central nervous system as short as possible, it is possible to reduce burden to a patient and injury to the central nervous system. In addition, the amount of wasted cells is liable to be relatively small. From the viewpoint of making the length of the portion from the front end to the discharge path 14 of the passage 11 to be as small as possible, it is preferably that the back end of the occlusion part 12 be positioned as posteriorly as possible, i.e., as close as possible to the discharge path 14. In addition, according to the above-mentioned viewpoint, it is most preferable that the back end of the occlusion part 12 be at the same position as the front end of the columnar part 14b.

EXAMPLES

The First Example to the Third Example of the above-discussed embodiment are explained below.

First Example

In the First Example, a puncture needle 1 was configured in the following dimension. Outer diameter of a needle body 10: about 1.5 mm. Inner diameter of a passage 11: about 0.5 mm. Distance from a front end of a front end part 13 to a central axis of a discharge path 14: about 1.4 mm. Distance between a tip of a connection part and a tip of the needle body: about 190 mm. Angle between one inclined surface and the other inclined surface of a frustoconical part 14a in FIG. 3(a): about 90° (degree). Inner diameter of a columnar part 14b: about 0.5 mm. Meanwhile, puncture needle S (Pittsburgh cell implantation cannula and stylette; Synergetics) and puncture needle M (biopsy/injection needle kit; Mizuho) were used as comparative examples. The puncture needle S has a front end part sharply formed and a discharge pot is formed at the front end and not at the side surface of the needle. The puncture needle M has a front end surface flatly formed and a discharge port is formed at a side surface of the needle that is 7 mm posteriorly away from the front end of the needle. In both puncture needles, the discharge path of a cell formed at the front end part is constant in terms of a surface area of a cross section orthogonal to a direction in which the discharge path extends regardless of a position regarding said direction. These puncture needles were used to carry out the following experimentation of flowing out water from the discharge port. Both puncture needles were disposed so that the height from the floor of an experimentation room to the discharge port would be the same with respect to one another and the aperture direction of the discharge port would substantially be in a horizontal direction. Furthermore, a syringe was connected to the back end of these puncture needles, and water was pressured into the puncture needle at a constant flow rate from the syringe so that the water would flow out from the discharge port of the front end part of each puncture needle. Furthermore, in the embodiment shown in FIG. 3, the angle between one inclined surface and the other inclined surface of the frustoconical part 14a is about 90°, but the present invention is not limited thereto. For example, the angle may be in the rage of about 45° to about 150°. In addition, the inner diameter of the columnar part 14b is about 0.5 mm and the inner diameter of the discharge port 15 is about 1.5 mm. However, the present invention is not limited thereto. The size may be any size that is equal to or less than the inner diameter of the columnar part 14b. For example, the inner diameter of the columnar part 14b is about 0.3 mm to about 1.2 mm. In addition, the inner diameter of the discharge port 15 may be any size that is equal to or less than the diameter of the needle body 10. For example, the inner diameter of the discharge port 15 is about 1.2 mm to about 1.6 mm.

FIG. 6 shows the result of experimentation using the puncture needle 1, FIG. 7 shows the result of experimentation using the puncture needle S and FIG. 8 shows the result of experimentation using the puncture needle M. All are results of when water is flowed into the puncture needle from a syringe at the flow rate of about 7 ml/minute. As shown in FIG. 6, water flowed out from the discharge port 15 of the puncture needle 1 so that the water would drop directly below the puncture needle. That is, the water flowing out from the discharge port 15 did not form a jet flow. Meanwhile, as shown in FIG. 7 and FIG. 8, a jet flow was formed by the water discharged from the discharge port of the comparative examples. FIG. 9 shows the result after repeatedly practicing the above-mentioned experimentation while changing the flow rate. The transverse axis of FIG. 9 is flow rate. The longitudinal axis is the distance from the position of the discharge port of the puncture needle to the furthest position where the water reached.

Second Example

In the Second Example, the puncture needle 1 used in the First Example was connected to a syringe with the capacity of about 1 ml. The syringe stored water (specifically, ultrapure water). Next, water was pressured into the puncture needle 1 from a syringe so that the water would flow out from the discharge port 15 of the front end part 13 of the puncture needle 1 while using a digital force gauge (ZTA-50N; Imada) to measure the force applied to the plunger of a syringe. The above-described measurement was carried out while increasing little by little the force applied to the plunger of the syringe until the water discharged from the discharge port 15 forms a jet flow. This causes fifty discharges of the minimal size of force generating a jet flow (hereinafter, referred to as the minimal jet flow formation force) regarding the puncture needle 1. As a result, as shown in FIG. 10, the average value of the minimal jet flow formation force of the puncture needle 1 was about 5.7 N. In addition, the same experimentation was carried out for each of the puncture needle S and puncture needle M in the First Example. As a result, as shown in FIG. 10, the average value of the minimal jet flow formation force of the puncture needle S was about 1.6 N. In addition, the average value of the minimal jet flow formation force of the puncture needle M was about 2.6 N. Furthermore, the above-described digital force gauge was used to measure the force that presses the plunger of the syringe in a state in which the puncture needle is not connected and, as a result, the force was about 1.0 N.

From the experimentation result above, it was found out that the puncture needle 1 of the present Example would not form a jet flow even when water is flowed in while applying any force within the range of about 5.7 N or less to the present syringe. In addition, according to the result of the puncture needle M with a large minimal jet flow formation force among conventional needles, it was found that the conventional minimal jet flow formation force is about 2.6 N. That is, it was found that a puncture needle that is less liable to form a jet flow compared to a conventional puncture needle is realized by configuring the puncture needle 1 of the present disclosure so that the minimal jet flow formation force would exceed about 2.6 N.

Third Example

In the Third Example, the puncture needle 1, puncture needle S and puncture needle M that were used in the First Example were used. In addition, a false brain for infusing liquid using a puncture needle was made as described below. Fist, saturated borax aqueous solution was diluted 3 times with hot water. The diluted borax aqueous solution was blended with laundry starch that was multiplied by 15 by being mixed with water. A product in which saturated borax aqueous solution and laundry starch were blended in such a manner was heated and poured into a container so that air would not be mixed in to prepare three spherical false brains. Furthermore, upon preparing the false brains, the stiffness of the false brains was adjusted by adjusting the concentration of the borax aqueous solution after dilution. If the false brain is too hard, even when liquid is tried to be infused into the false brain using the puncture needle, there would be a problem of leakage from the gap between the needle and the false brain. In addition, if the false brain is too soft, there would be a problem of liquid infused into the false brain with the puncture needle rising to the upper part of the false brain by the difference in the specific gravity with respect to the false brain. The false brain would have suitable stiffness by diluting the saturated borax aqueous solution three times, wherein the above-described problems did not occur.

Each of the puncture needle 1, puncture needle S and puncture needle M connected to a syringe is inserted into the three prepared false brains about 3 cm deep from the tip of the needle. Furthermore, Wright-Giemsa staining liquid that was diluted about three times from the stock solution is flowed into each puncture needle for about 30 seconds from a syringe at each flow rate of about 200, about 500, about 1000 and about 2000 µl/minute. As a result, as shown in FIG. 11, when the flow rate was about 2000 µl/minute, a projecting part, projecting downwards in the puncture needle S and sideways in the puncture needle M, was formed at the false brain. It is considered that this happened because liquid discharged from the discharge port of each puncture needle formed a jet flow and this jet flow caused great pressure to be applied to the false brain. Meanwhile, a projecting part was not formed in the puncture needle 1 even when the flow rate was about 2000 μl/minute and the false brain was shown to be substantially spherical. It is considered that this was because a jet flow was not formed like in the puncture needles S and M.

Second Embodiment

A second embodiment which is another embodiment of the present disclosure is explained below. The second embodiment is regarding the puncture needle kit 100 shown in FIG. 12. The puncture needle kit 100 comprises a puncture needle 1 of the first embodiment, a container 101 storing a cell and an unravelling needle 102 for unravelling cells. The container 101 stores a cell together with liquid such as saline and culture liquid. The container 101 may be provided with a device for maintaining the inside in a state suitable for delivery of a cell (temperature, position and the like). The unravelling needle 102 has an aperture that would be a circulation port for a cell at both ends and is a cylindrical member where a passage for a cell to be communicated between the apertures of both ends is formed inside. The aperture and passage of the unravelling needle 102 are adjusted to a size so that condensed cells would be unraveled into a state in which the cells are separated to a certain extent upon circulating the cells. For example, a cell within the container 101 is sucked up into a syringe through the unravelling needle 102 connected to the syringe. Alternatively, a cell once stored in a syringe is flowed out to the outside of the syringe through the unravelling needle 102 connected to the syringe. At least any of the above would unravel cells in a condensed state and be able to achieve a state in which the cells are separated to a certain extent. When said unraveled cells are transplanted into a brain using the puncture needle 1, the cells are less liable to be clogged inside the puncture needle 1 compared to the case in which cells in a condensed state are used. Thus, there is lower fear of a cell and liquid discharged from the discharge port 15 of the puncture needle 1 forming a jet flow.

Modified Example

While the above is an explanation regarding a suitable embodiment of the present disclosure, the present disclosure is not limited to the above-discussed embodiment and can be changed in various ways only in the scope of matters described in the Solution to Problem.

For example, instead of the discharge path 14 of the above-discussed embodiment, any of the discharge paths 24, 34, 44 and 54 shown in FIG. 13(*a*) to FIG. 13(*d*) may be formed at the front end part of the needle body. The discharge path 24 is a passage for a cell linking the passage 11 and the discharge port 15 as shown in FIG. 13(*a*). The inner surface of the discharge path 24 is bent in a curved-like manner in the cross section shown in FIG. 13(*a*). The discharge path 24 is formed so that a surface area of a cross section orthogonal to the upward/downward direction (the direction in which the discharge path 24 extends) would increase in size in approximately two phases towards the discharge port 15 within the range surrounded by the dashed line E. The dashed line E shows the range that can define the cross section of the discharge path 24 in the same manner as the above-discussed embodiment.

By achieving the discharge path 24 of FIG. 13(*a*), it becomes possible to accumulate cell liquid in a widened portion and then take the cell liquid outside, thereby enabling jet flow formation to be even weaker by this part being an interference site even when a jet flow is made therebelow. In the embodiment shown in FIG. 13(*a*), a discharge path is an approximately columnar part with sizes in two phases, but the present invention is not limited thereto. For example, at least one may be an approximately columnar part, or may be an approximately frustoconical part. In addition, the phases may be three phases or more.

In FIG. 13(*a*), for example, the inner diameter of the first approximately columnar part is about 0.3 mm to about 1.2 mm and the inner diameter of the second approximately columnar part is about 1.2 mm to about 1.6 mm.

As shown in FIG. 13(*b*), the discharge path 34 is a passage for a cell linking the passage 11 and the discharge port 15. Regarding the discharge path 34, a surface area of a cross section orthogonal to the upward/downward direction in any position regarding the upward/downward direction (the direction in which the discharge path 34 extends) is also equal to or greater than a surface area of a cross section of a position closer to the passage 11 than said position within the rang surrounded by a dashed line E. The dashed line E shows a range that can define a cross section of the discharge path 34 in the same manner as the above-discussed embodiment. The discharge path 34 consists of a substantially column-like columnar part 34*a* and a substantially frustrum-like frustoconical part 34*b*. The upper end of the columnar part 34*a* is connected with the discharge port 15 and the lower end of the columnar part 34*a* is connected with the upper end of the frustoconical part 34*b*. The lower end of the frustoconical part 34*b* is connected with the passage 11. The frustoconical part 34*b* is formed so that a surface area of a cross section orthogonal to the upward/downward direction would increase smoothly towards the discharge port 15 within the range surrounded by the dashed line E. By achieving the discharge path 34 of FIG. 13(*b*), the discharge path 34 would have a widened portion at a tip where jet flow is prevented in a fan shape, thereby being able to doubly prevent a jet flow. For example, the smallest inner diameter of the frustoconical part is about 0.3 mm to about 1.2 mm and the maximum inner diameter of the frustoconical part and the inner diameter of the columnar part is about 1.2 mm to about 1.6 mm.

As shown in FIG. 13(*c*), the discharge path 44 is a passage for a cell linking the passage 11 and the discharge port 15. Regarding the discharge path 44, a surface area of a cross section orthogonal to the upward/downward direction in any position regarding the upward/downward direction (the direction in which the discharge path 44 extends) is also equal to or greater than a surface area of a cross section of a position closer to the passage 11 than said position within the range surrounded by a dashed line E. The dashed line E shows the range that can define a cross section of the discharge path 44 in the same manner as the above-discussed embodiment. The discharge path 44 consists of a substantially column-like columnar parts 44*a* and 44*c* and a substantially frustrum-like frustoconical part 44*b*. The upper end of the columnar part 44*a* is connected with the discharge port 15 and the lower end of the columnar part 44*a* is connected with the upper end of the frustoconical part 44*b*. The lower end of the frustoconical part 44*b* is connected with the upper end of the columnar part 44*c*. The frustoconical part 44*b* is formed so that a surface area of a cross section orthogonal to the upward/downward direction increases towards the discharge port 15. The lower end of the columnar part 44*c* is connected with the passage 11. By achieving the discharge path 44 of FIG. 13(*c*), an aperture part can be made wider than the discharge path 34 of FIG. 13(*b*) and thus it is possible to further prevent the danger of a cell being clogged. For example, the minimum inner diameter of the frustoconical part and the inner diameter of the columnar part 44*c* are about 0.3 mm to about 1.2 mm and the maximum inner diameter of the frustoconical part and the inner diameter of the columnar part 44*a* are about 1.2 mm to about 1.6 mm.

As shown in FIG. 13(*d*), the discharge port 54 is a passage for a cell extending from the passage 11 to the discharge port 15 along an α direction anteriorly inclined with respect to the upward/downward direction (dashed line). The inclination angle θ in the α direction with respect to the upward/downward direction (dashed line) may be any angle. For example, the angle is over about 0° and is about 30°, preferably about 10° to about 20°. The entirety of the discharge path 54 has a substantially conical shape. The discharge path 54 is formed so that a surface area of a cross section orthogonal to the α direction increases smoothly towards the discharge port 15. Furthermore, a cross section of the discharge path 54 is defined within the range surrounded by the dashed line E' of FIG. 13(*d*). The dashed line E' corresponds to a range excluding a range in which the discharge port 15 is formed and a range in which an aperture 54*c* of the discharge path 54 to the passage 11 is formed regarding the α direction. The minimum inner diameter of the discharge path 54 is about 0.3 mm to about 1.2 mm and the inner diameter of the discharge port is about 0.3 mm to about 1.2 mm.

By achieving the discharge path 54 shown in FIG. 13(*d*), it is possible to prevent brain tissue from entering into the puncture needle 1 upon advancing the puncture needle 1 inside a brain.

In addition, regarding the puncture needle 1 of the above-discussed embodiment, the front end surface 13*a* of the front end part 13 has a hemispherical shape. However, the front end surface 13*a* may have any shape as long as the front end surface 13*a* is curved and anteriorly projecting. For example, the front end surface 13*a* may be along an ellipsoid or paraboloid.

In addition, in the above-discussed embodiment, the front end 15*a* of the discharge port 15 is positioned between a boundary B between the front end surface 13*a* and the side surface 13*b*. However, the front end 15*a* of the discharge port 15 may be positioned posterior to the boundary B between the front end surface 13*a* and the side surface 13*b*.

In addition, in the above-discussed embodiment, use of the puncture needle 1 for transplanting a cell such as a stem cell to a specific position of a brain is assumed in stereotactic brain surgery for treating brain infarction. However, the puncture needle 1 may be applied to other central nervous system, i.e., spinal cord. In addition, the puncture needle 1 may be used for the purpose of infusing an object with fluidity other than a cell such as liquid agent into a central nervous system.

Example 4: Cell Administration

An Example of cell administration is described below. If necessary, an animal used in the following Example is handled while observing the standard stipulated by Hokkaido University and based on the Declaration of Helsinki and GCP.

The following surgery is carried out using the needle prepared in each of the above-described embodiments.

(1) Insertion of Needle

In the present Example, a bone marrow stem cell is used as an object having fluidity.

After receiving a cell, suitable liquid (may be a culture medium for a cell, saline, or the like) is sufficiently suspended to break a cell cluster. An 18G needle is used as a 1 ml injection needle for insulin and the needle of the present invention is used to suck cell suspension liquid into a syringe. Upon doing so, a needle to be transplanted is mounted from the posterior. Specifically, an inner cylinder is attached to an outer cylinder for injection and cell liquid is filled to the tip so as to remove the air inside. The needle is advanced to a stopper in accordance with the angle of Leksell frame that was set beforehand. In such a manner, it is confirmed that a guide stop is at a suitable position (e.g., may be 0 mm, or may be −7 mm). Upon advancing a needle, the needle is advanced while being rotated so as not to cause injury to a brain blood cell. That is, after wetting the tip, the needle is advanced while slowly being rotated for five minutes or longer. In this regard, the suitable position can be suitably changed depending on the position of the hole. For example, when a needle to be used has a hole from which a cell exits that is present at a place that is 7 mm from the tip of the needle, while a cell can be administered at a periphery of a target when punctured at ±0 mm, a brain tissue would be pierced 7 mm deeper than planned. Thus, it can be considered that a cell can fill the space where the needle has passed by pulling out the needle, and it is possible to achieve an actual site where the cell reaches even when the location where the cell exits still has 7 mm to reach the intended target. When a needle to be used is provided with a fan-shaped hole where a cell exists substantially near the tip, it is possible to employ ±0 mm.

(2) Cell Administration

When an intended location is reached (i.e., a cell is administered upon touching a stopper), a 1 ml syringe with a cell inside is attached and slowly administered for five minutes or longer (as one example, a high dose is fifty million cells/1000 μl). The needle is pulled about 3 mm out to the front (−10 mm) at the point when 200 μl is inside. This causes the cell to remain centering around a cavity where the needle was pierced. Herein, 200 μl is administered again. A dead cavity of a needle is about 20 μl, which is within the scope of a margin of error. Then, the needle is left to stand at this location for five minutes, and then the needle is pulled out.

(3) Closing Incision

Gelfoam (medical gelfoam, sterile absorbable gelatin preparation which is a hemostatic agent; obtainable from Pfizer or the like) and fibrin glue (Bolheal® that can be obtained from Teijin, periplast that can be obtained from CSL Behring) are placed at the surface of the hole, wherein flow-out of a cell is prevented (i.e., so that the pressure would not cause flowback of a cell that was deeply put in from the punctured hole upon pulling out the needle). In addition, a dura mater is filled with gelfoam (herein, a Burr hole cap is not used to decrease an infection risk). This causes the opened hole to be replaced with gelfoam (replaced with a fibroblast in the future).

(4) Result

As a result of the above, a cell is successfully infused into a brain.

Although the present disclosure has been exemplified using a preferable embodiment of the present invention as described above, it is understood that the scope of the present disclosure should be interpreted by the Claims alone. It is also understood that any patent, any patent application, and any references cited herein should be incorporated herein by reference in the same manner as the contents are specifically described herein.

INDUSTRIAL APPLICABILITY

The present disclosure is advantageous in being able to provide a puncture needle, a puncture needle kit and a stereotactic brain surgery device, wherein an object such as liquid discharged from a discharge port is less liable to form a jet flow and a central nervous system is less liable to be injured.

1 Puncture needle
3a Front end surface
10, 10' Needle body
11 Passage
13 Front end part
13a, 13'a Front end surface
13b Side surface
14, 14', 24, 34, 44, 54 Discharge path
15, 15' Discharge port
15a Front end

The invention claimed is:

1. A puncture needle kit, comprising:
a puncture needle for infusing an object with fluidity into a brain, the puncture needle comprising:
  a needle body along a forward/backward direction, wherein a passage for the object is formed inside;
  a discharge port of the object formed at an outer surface of a front end part of the needle body;
  a discharge path connecting the passage to the discharge port, characterized in that:
the needle body is a single tube comprising the passage;
  a surface area of a cross section of the discharge path orthogonal to a direction in which the discharge path extends from the passage to the discharge port is increased smoothly from a side of the discharge path that the passage is on towards the discharge port in at least one part of the discharge path and, in each position regarding the direction in which the discharge path extends from the passage to the discharge port, is equal to or greater than a surface area of the cross section in a position closer to the passage,
  the outer surface of the front end part comprises: a front end surface anteriorly projecting while smoothly bending; and a cylindrical side surface connected with the front end surface, a front end of the discharge port is positioned posterior to a front end of the passage and is positioned at a boundary between the front end surface and the cylindrical side surface or positioned posterior to the boundary,
  wherein the discharge path comprises a columnar part linked to the passage and a frustoconical part connecting the discharge port and the columnar part,
  wherein an inner diameter of the passage is about 0.3 mm to about 1.2 mm, an inner diameter of the columnar part is about 0.3 mm to about 1.2 mm, and a frustoconical angle of the frustoconical part is about 90°,
  wherein the discharge path further comprises a second columnar part connected to the discharge port and the frustoconical part,
  wherein an inner diameter of the discharge port and a maximum inner diameter of the frustoconical part are about 1.2 mm to about 1.6 mm, characterized in that the object comprises a cell;
a container storing the object that comprises a cell preparation containing cells and a liquid containing culture medium for a cell or saline; and
an unravelling needle.

2. A puncture needle kit, characterized by comprising:
puncture needle for infusing an object with fluidity into a brain, the puncture needle comprising:
  a needle body along a forward/backward direction, wherein a passage for the object is formed inside;
  a discharge port of the object formed at an outer surface of a front end part of the needle body;
  a discharge path connecting the passage to the discharge port, characterized in that:
the needle body is a single tube comprising the passage;
  a surface area of a cross section of the discharge path orthogonal to a direction in which the discharge path extends from the passage to the discharge port is increased smoothly from a side of the discharge path that the passage is on towards the discharge port in at least one part of the discharge path and, in each position regarding the direction in which the discharge path extends from the passage to the discharge port, is equal to or greater than a surface area of the cross section in a position closer to the passage,
  the outer surface of the front end part comprises: a front end surface anteriorly projecting while smoothly bending; and a cylindrical side surface connected with the front end surface,
  a front end of the discharge port is positioned posterior to a front end of the passage and is positioned at a boundary between the front end surface and the cylindrical side surface or positioned posterior to the boundary,
  wherein the discharge path comprises between the passage and the discharge port, from a side of the discharge path that the passage is on towards the discharge port, a columnar part with a first size and a frustoconical part or a columnar part connected to the discharge port with a second size that is greater than the first size,
  wherein the first size and the second size are the surface area of a cross section of the discharge path orthogonal to the direction in which the discharge path extends from the passage to the discharge port,
  wherein the first size is about 0.3 mm to about 1.2 mm and the second size is about 1.2 mm to about 1.66 mm, characterized in that the object comprises a cell;
a container storing the object that comprises a cell preparation containing cells and a liquid containing culture medium for a cell or saline; and
an unravelling needle.

* * * * *